United States Patent [19]

Ribalta et al.

[11] Patent Number: 4,495,199
[45] Date of Patent: Jan. 22, 1985

[54] DIOXOLANIC AMINE WITH PHARMACOLOGICAL ACTIVITY, ITS METHOD OF PREPARATION, THE PHARMACEUTICAL COMPOSITIONS CONTAINING SAME AND THEIR USE IN HUMAN MEDICINE

[76] Inventors: José Miguel B. Ribalta, 125 bis, calle Mayor de Sarriá ; Leonida Bruseghini, 5, calle Caponata, both of Barcelona, Spain; Silvano Casadio, 11, via Tantardini, Milan; Italy; Jorge P. Iniesta, 39, calle Leyva, Barcelona, Spain

[21] Appl. No.: 432,397

[22] Filed: Sep. 30, 1982

[51] Int. Cl.$^3$ ............... A61K 31/34; C07D 317/00
[52] U.S. Cl. ............................ 514/467; 549/448; 514/465
[58] Field of Search ............... 549/448; 424/285, 278

[56] References Cited

U.S. PATENT DOCUMENTS 3,972,900  8/1976  Fothergill et al. ............ 549/448
4,237,144  12/1980  Cragoe, Jr. et al. ......... 424/285 X Primary Examiner—Ethel G. Love
Attorney, Agent, or Firm—Michael J. Striker

[57] ABSTRACT

A new dioxolanic amine is disclosed, with pharmacological activity of the following structural formula I:

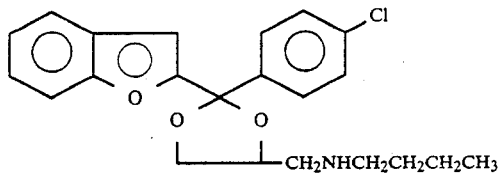

as well as its pharmaceutically acceptable salts, possessing intense vasodilatory, anti-angina and anti-arrhythmic activity, accompanied by a low toxicity; its method of preparation; pharmaceutical compositions containing the said compounds; and the treatment and prevention various pathological conditions with the use of said compositions. Also disclosed are new dioxolanic compound of the following structural formula II:

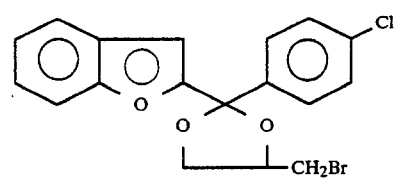

which is an intermediate compound in the preparation of the formula I compound; and its method of preparation.

5 Claims, No Drawings

DIOXOLANIC AMINE WITH PHARMACOLOGICAL ACTIVITY, ITS METHOD OF PREPARATION, THE PHARMACEUTICAL COMPOSITIONS CONTAINING SAME AND THEIR USE IN HUMAN MEDICINE

BACKGROUND OF THE INVENTION

The present invention relates to a compound which has been given the abbreviated name ITA 362.

The inventors succeeded in obtaining the said product ITA 362 for the first time in the course of a chemical and pharmacological study of new molecules of the general formula

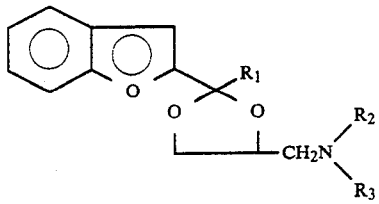

VI where $R_1$ is methyl, phenyl or p-chlorophenyl, and $R_2$, $R_3$ hydrogen, alkyl, hydroxyalkyl, cycloalkyl, aryl, guanidin, dimethylguanidin. About sixty new molecules have been obtained in this work.

The search for chemical procedures which would make it possible to obtain the aforesaid compounds of the general formula VI was a very laborious and complicated one, since the unfavourable conditions of the reaction for obtaining the bromomethyl derivative of formula II

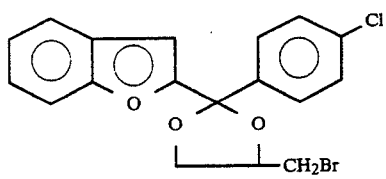

II required ample, extensive and difficult study. Specifically, the difficulty is due to the fact that it is necessary to use an excessive amount of epibromhydrine to bring about this reaction. The problem then arises that this reagent, i.e. the epibromhydrine, polymerizes and produces reaction mixtures which are very difficult to purify. To overcome these obstacles, it was necessary to find the combination of proportions, temperature, time and catalyst which would make it possible to obtain with only one distillation a product of sufficient quality to be used in the next reaction.

The said chemical research work was finally successful, in that synthesis was achieved of a large number of compounds of formula VI.

In view of the chemical structure of these formula VI compounds, the inventors hoped to discover interesting pharamacological properties in some of them. Specifically, the original design of formula VI was created by combining into a single molecule two structures which have been shown to possess good vasodilatory or anti-angina activity. One is the benzofuranic structure, common to drugs presently in use such as Amiodarone (Inventors: Touder, Bidon; U.S. Pat. No. 3,248,401) and Benziodarone (Inventors: Buu-Hoi, Beaudet; U.S. Pat. No. 3,012,042). The other structure is the dioxolanic rest, common to molecules being researched such as 2,2-dimethyl-4-hydroxymethyl-1,3-dioxolane (Researchers: Melson et col.; Acta Biol. Med. 395 (1961)), and which are also part of known drugs such as Guanadrel (Inventors: Hansson et col.; Clin.Pharmac.Therap. 14,204 (1973)).

With the described design of the molecule of formula VI, the inventors combined into a single molecule different pharmacological activities, namely: anti-arrhythmic, vasodilatory and anti-angina, which in conjunction with low toxicity could constitute a useful drug for treating the circulatory diseases, principally those affecting the heart.

The inventors have in fact succeeded in obtaining pharmacologically interesting formula VI products. For example, when $R_2$, $R_3$ is guanidin or dimethylguanidin, a group of compounds is obtained of such pharmacological importance that they were presented at the II National Congress of the Spanish Chemical Therapy Society, held in Madrid in 1982.

Accordingly, it is clear that the initial work of chemical nature attempting to achieve synthesis of formula VI products was begun with the clear intention of discovering interesting pharmacological properties in these products.

In this research process, the outstanding product in terms of its excellent pharmacological properties was the one called ITA 362, which is a formula VI product in which $R_1$ is p-chlorophenyl, $R_2$ is hydrogen and $R_3$ is n-But, in other words, the product of formula I

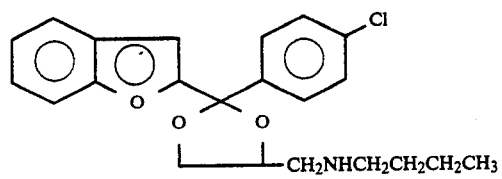

I which is the object of this invention.

SUMMARY OF THE INVENTION

This invention involves a new dioxolanic amine with pharmacological activity which has been allocated the reference ITA 362, for brevity.

This new compound has the following formula I

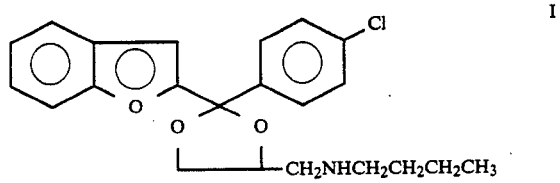

I corresponding to 2-(2'-benzofurani)-4-n-butylaminomethyl-2-p-chlorophenyl-1, 3-dioxolan.

Also within the scope of this invention are the pharmaceutically acceptable salts of the compound ITA 362, such as maleate, citrate, orotate, oxalate, malonate, p-toluensulphate and the like.

The present invention additionally encompasses the method of preparation of the aforementioned compounds and pharmaceutical compositions including them as active agent.

Finally, inasmuch as the starting product used for preparation of ITA 362 was also first discovered in connection therewith, as was the method of preparing the starting product, these two are included within the scope of the present invention. The new compound ITA 362 possesses intense vasodilatory, anti-angina and anti-arrhythmic activity, accompanied by a low toxicity.

As will be explained in detail further on in the description of the chemical synthesis, in order to prepare the compound ITA 362 one starts off from the dioxolanic bromomethyl derivative of Formula II, which has the following structure:

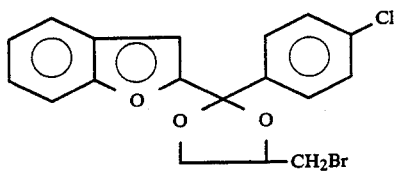

II

In fact this compound II, 2-(2'-benzofuranil)-4-bromomethyl-2-p-chlorophenyl-1,3-dioxolan, was obtained for the first time by the same inventors during the course of the research that led to the preparation of the compound ITA 362.

The compound according to the invention, 2-(2'-benzofuranil)-4-n-butylaminomethyl-2-p-chlorophenyl-1,3-dioxolan, is recommended for the treatment of angina pectoris, stenocardia and acute visceral pain; prophylaxis of the effort, stress, and nocturnal angor; treatment in the recuperation stage of miocardiac infarction; ventricular insufficiency of left side congestion; pulmonary oedema; supra-ventricular and ventricular arrythmia or arrythmia resistant to the classic treatments; sinus tachycardia and paroxysmal tachycardia; auricular and flutter fibrillation; nodal and ventricular tachycardia; ventricular and auricular extrasystoles and the Wolf-Parkinson-White syndrome. It may also be used as indicated during heart surgery or anesthesia.

The daily dose of the active pharmaceutical product may vary over a wide margin between 5 and 1000 mg depending on the therapeutic application and the form of administration.

The new product ITA 362 described above, obtained by means of the method according to the present invention, may be administered in the various conventional forms such as, for example, by tablets, dragees, capsules or in suspension with a view to administration orally or by intravenous injection.

The pharmaceutical specialty contains the active compound and one or other of the acceptable pharmaceutical vehicles, auxiliary non-toxic substances such as dispersal agents, compacting agents, emulsifiers, preservatives, humectants or others with particularly desirable specific properties. The following serve as non-limititive illustrative examples of suitable pharmaceutical specialties containing the active product prepared according to the present invention:

EXAMPLE 1

Capsules (containing 200 mg of active ingredient)

| 1 Capsule No. 1 | |
| --- | --- |
| 2-(2'-benzofuranil)-4-butylaminomethyl-2-p-chlorophenyl-1,3-dioxolane, maleate | 200 mg |

-continued

| 1 Capsule No. 1 | |
| --- | --- |
| Lactose USP (USP — United States Pharmacopea) | 45 mg |
| Magnesium stearate | 5 mg |
| | 250 mg |

EXAMPLE 2

Tablets (with 25 mg of active ingredient)

| | |
| --- | --- |
| 2-(2'-benzofuranil)-4-butylaminomethyl-2-p-chlorophenyl-1,3-dioxolane, maleate | 25.0 mg |
| Starch USP | 2.5 mg |
| Talc USP | 2.0 mg |
| Magnesium stearate | 0.5 mg |
| | 30.0 mg |

The compound ITA 362 as in formula I is synthesized chemically by means of a two-stage process, as outlined below:

(a) first stage: having for its object the preparation of formula II that is, 2-(2'-benzofuranil)-4-bromomethyl-2-chlorophenyl-1,3-dioxolane;

(b) second stage: having for its object the preparation of the compound ITA 362 starting off from formula II.

Nevertheless, both stages, first and second, though having their individual identities, together from one unity of invention. The two stages are described in detail further on.

First Stage

The preparation of the bromomethyl dioxolanic derivative of formula II, that is, the 2-(2'-benzofuranil)-4-bromomethyl-2-p-chlorophenyl-1,3 dioxolane, starts with the Ketone of Formula III

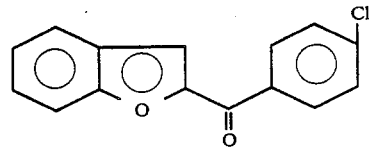

III in a reaction of which the scheme is the following:

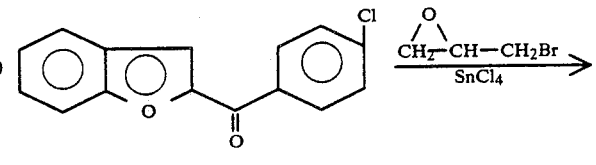

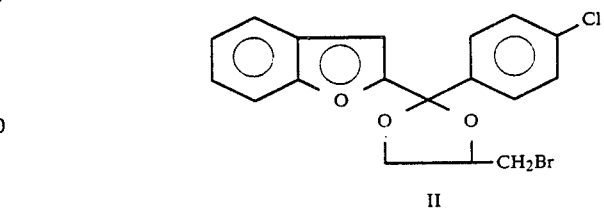

To a solution of Ketone III in a chloro solvent such as methylene chloride, chloroform or carbon tetrachloride, epibromhydrene is added at low temperature, (preferably about 0.5° C.), in a quantity of between 1 and 3 times mol. with respect to the Ketone III of epibromhydrine. Then the catalyst corresponding to a Lewis acid (preferably tin tetrachloride, boron trifluoride or anhydrous aluminium trichloride) is slowly added in a quantity on the order of one tenth part mol. with respect to the epibromhydrine, with maintenance of a low mixture temperature during the addition.

Reaction is then completed at a temperature of between the ambient and that of the boiling point of the mixture over a suitable time period (from 2 to 24 hours).

After completion of the reaction, a solution of sodium or potassium hydroxide is added quickly up to basic pH. Then follows decanting, washing, drying and removing the solvent of the organic phase, after which the residue thus obtained is distilled at a reduced pressure.

The structure of the new product corresponds to 2-(2'-benzofuranil)-4-bromomethyl-2-p-chlorophenyl-1,3-dioxolane, which has two isomers due to the rigidity produced in the molecule by the dioxolanic ring. These isomers are reflected by the nuclear magnetic resonance signal of the furanic proton.

This type of isomer is described in great detail for similar systems by P. Calinaud and J. Gelas (Bull. Soc. Chem. Fr. 5–6, 1228–1236 and 1237–1242, 1975) and taking as the principal substituent in the position 2 of the dioxolanic ring the benzofuranil residue, the structures IV and V as shown in the following schemes, are formed:

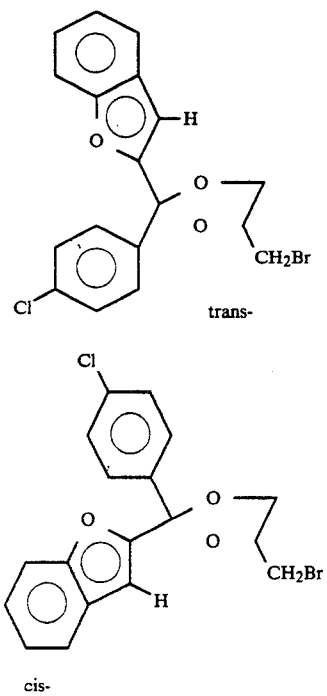

transcis-

The product so obtained is used for the following or second stage.

Second Stage

The preparation of the ITA 362 is done starting from the 2-(2'-benzofuranil)-4-bromomethyl-2-p-chlorophenyl-1,3-dioxolane of formula II, as follows:

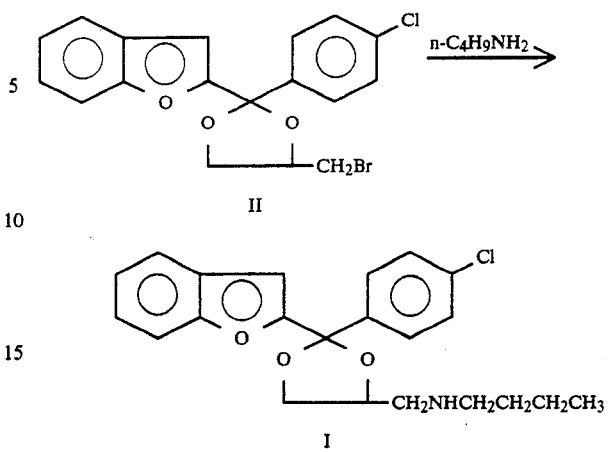

The 2-(2'-benzofuranil)-4-bromomethyl-2-p-chlorophenyl-1,3-dioxolane is caused to react with n-butylamine in an inert anhydrous solvent such as benzene, toluene or xylene at the boiling point temperature of the mixture during the time required to complete the reaction (from 5 to 50 hours) and in the presence of an acidity acceptor. As the acidity acceptor the same n-butylamine may be used, using at least 2 mols of this for each mol of the bromomethyl derivative. Equally suitable for use as acidity acceptor is a tertiary amine, such as e.g. triethylamine or pyridine, or even an inorganic base, such as e.g. anhydrous sodium or potassium carbonate.

After the reaction is completed, a solution of sodium or potassium hydroxide is added quickly, followed by decanting, washing, drying and removing the solvent of the organic phase, thus yielding the product in the form of a reddish-yellow oil which can be purified by distillation at a low pressure. Treatment with an acid, preferably a weak organic acid such as e.g. maleic, citric, orotic, fumaric, malonic, acetic, p-toluen-sulphonic or similar acid, in a suitable organic solvent such as e.g., acetone, methanol, ethanol, isopropanol, chloroform, ethyl acetate, benzene, or in general any organic solvent which would adequately dissolve the dioxolanic compound, allows one to obtain a saline solidederivative which is more convenient for future handling and use. When the acid used has at the same time geometric or optical isomerism, as is the case with maleic and fumaric acid, upon the formation of the corresponding salts one can separate the two diastereoisomers which may be present by fractional crystallization, thus obtaining in this manner the resolution of the isomers.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Preliminary Example (First Stage)

Below is described an example for the preparation of the 2-(2'-benzofuranil)-4-bromomethyl-2-p-chlorophenyl-1,3-dioxolane.

109 g (0.80 m) of epibromhydrine is added to a solution of 136 g (0.53m) of p-chlorobenzoyl-2-benzofurane in 2000 cc of anhydrous chloroform, at 0–5 deg. C. 9.4 cc (0.08 m) of tin tetrachloride dissolved in 35 cc of anhydrous chloroform is then added slowly (45 minutes).

Having terminated the addition above, the preparation is allowed to reach room temperature during 15 hours of stirring. By means of TLC (thin-layer chromotography, eluent: benzene/hexane 4:1) the progress of the reaction can be controlled.

32 g of NaOH dissolved in 100 cc of water are then quickly added, ensuring that the final pH is basic, after which 30 minutes of stirring is performed. Decanting, washing the organic phase with water until the washings are neutral pH, drying the chloroformic solution with Na₂SO₄ and eliminating the solvent at a low pressure, one obtains a yield of 224 g of a yellowish oil.

Molecular distillation at 145 deg. C. and approximately $10^{-2}$ mm Hg, yields 143 g (69%) of a slightly yellow oil. A further distillation of the residue of the previous operation yields a further 41 g. (total yield: 88%). The product identifies as follows:

Halogens: (Schöninger): experimental=28.84; theoretical: 29.30.

IR (film): Characteristic bands at 1595, 1490, 1450, 825 and 750 cm$^{-1}$.

NMR (CDCl₃): δ=7.75–6.85 (m,8, aromatics); 6.65 and 6.55 two singlets corresponding to the furanic proton for the cis- and the trans-isomers; 4.80–3.20 (m,5, aliphatics).

The experimental ratio of the aliphatic/aromatic integrals (theoretical; 0.555) is a very significant analytic measurement for testing the quality of the resulting product. EM: Molecular peak at m/e 392 and 394 with an isotopic ratio suiting a bromo atom and a chloro atom.

The product so obtained is ready for the aforementioned second stage leading to the preparation of the 2-(2'-benzofuranil)-4-n-butylaminomethyl-2-p-chlorophenyl-1,3-dioxolane. Should in any instance the reaction has not been complete, most of the unreacted product may be eliminated by precipitation with cyclohexane and, if necessary, carrying out a previous distillation at 130 deg. C. and $10^{-2}$ mm Hg to remove the more volatile components.

Examples of the preparation procedure for obtaining the new dioxolanic amine of formula I (ITA 362) and its salts are described below, this being the second stage, with all the details not affecting the essentiality of the invention being variables and in no way meant to be limitative of the same.

EXAMPLE 3

Preparation of the 2-(2'-benzofuranil)-4-n-butylaminomethyl-2-p-chlorophenyl-1,3-dioxolane (reference ITA 362)

A solution of 266 g (0.676 m) of 2-(2'-benzofuranil)-4-bromomethyl-2-p-chlorophenyl-1,3-dioxolane and 400 cc (4.06 m) of n-butylamine in 1000 cc of anhydrous toluene is set to boil during 30 h. By means of TLC (thin-layer chromatography, eluent AcOEt) the progress of the reaction can be controlled. The sollution is allowed to cool, after which 300 cc of NaOH (2N) are quickly added, followed by stirring during 30 minutes. After decanting, then thoroughly washing the organic phase with water to remove the excess n-butylamine, and eliminating the solvent at a low pressure, 255 g (98%) of a very thick reddish oil are obtained.

This product is of a quality suitable for the subsequent preparation of the salts. If required, a further purification carried out by molecular distillation, at 175 deg. C. and 3–4.10$^{-2}$ mm Hg, yields 221 g (85%) of a very thick yellowish oil.

Potentiometric evaluation of basic groups: 103%.

IR (film): characteristic bands at 1600, 1450, 1250, 1090, 830 and 755 cm$^{-1}$.

NMR (CDCl₃):δ=7.80–6.85 (m, 8, aromatics); 6.70 and 6.55 two singlets corresponding to the furanic proton for the cis- and trans-isomers; 4.80–3.80 (m, 3,

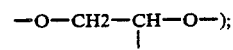

3.00–2.45 (m, 4, —C̲H̲₂NH —C̲H̲₂); 1.80–0.70 (m, 7, —C̲H̲₂C̲H̲₂C̲H̲₃).

The aminic proton may appear as a singlet with δ approx. 2.2–2.5 or even included within the other signals in this zone in the form of a wide signal.

EM: molecular peak at m/e=385.

The preparation of salts of the 2-(2'-benzofuranil)-4-n-butylaminomethyl-2-p-chlorophenyl-1,3-dioxolane (ITA 362)

Because the ITA 362 base is an oil, it is more convenient for its manipulation and usage to be converted to a solid salt by treating it with a suitable acid. Due to the instability of the dioxolanic compounds in an aqueous medium it is preferable to use for its salification weak acids such as e.g. maleic, citric, orotic, acetic, fumaric, oxalic, malonic, p-toluensulphonic, or similar, in any adequate organic solvent such as e.g. acetone, methanol, ethanol, isopropanol, chloroform, ethyl acetate, benzene and, in general, any solvent which would adequatly dissolves the amine.

When the acid used has at the same time geometric or optical isomerism, in the formation of the corresponding salt one of the two diastereoisomers may be preferably separated by crystallization. Such is the case with maleate, the preparation of which is detailed below by way of example, with the analytical physical data of the other salts as well.

EXAMPLE 4

Preparation of the maleate of the ITA 362

To a solution of 166 g (0.43 m) of ITA 362 in 400 cc of acetone at 40–50 deg. C. is added 50 g (0.434 m) of maleic acid dissolved in acetone at the same temperature. The mixture is stirred and immediately a white solid starts separating out until it forms a compact mass. After allowing the solid to cool, filtering it, washing it with acetone and vacuum drying on CaCl₂, 134 g (62%) of a white crystalline solid are obtained. Melting point: (m.p.) 163–164 L deg. C.

Potentiometric evalutation of the acid groups: 100.0%

Potentiometric evaluation of the basic groups: 101.0%

IR (KBr): characteristic bands at 1580, 1480–1450, 1360, 1090, 1020–970 and 760 cm$^{-1}$.

NMR (d₆-DMSO): The spectrum with minor variations in the displacement and in the form of the signals is very similar to that of ITA 362 base, except for a new signal at 6.3 ppm corresponding to the olefin protons of the maleic acid, and signals of furanic proton which appear as two singlets at 6.70 and 6.55 ppm in the free base. While in the base both signals have a similar intensity, with only the most deshielded being slightly more intense (10–20%), in the salt this signal clearly predominates with respect to the other in a proportion of 3:1.

Concentrating the mother liquid until almost dryness and crystallizing anew with ethyl acetate, one obtains 38 g (18%) of a white crystalline solid. m.p.: 143–143.5 deg. C.

Potentiometer evaluation of the acid group: 100.8%
Potentiometric evaluation of the basic group: 99.1%
IR (KBr): A spectrum very similar to that of the first fraction with minor variations, though significant, in the form and the intensity of the bands.
NMR ($d_6$-DMSO): A spectrum practically identical to the first fraction except for the signals corresponding to the furanic proton. In this case the signal at 6.55 ppm undoubtedly predominates, in the proportion of 4:1.

EXAMPLE 5

Preparation of orotate of the ITA 362

On heating with reflux in ethanol a stoichiometric mixture of the ITA 362 base and orotic acid, a white crystalline solid separates out in parallel with the transformation of the acid that previously has not completely dissolved.

m.p.: 235–6 deg. C. (d).
IR (KBr): characteristic bands at 1710, 1630, 1410, 1100 and 775 cm$^{-1}$.

Working in a manner generally similar to that indicated above, and in accordance with well established techniques, one obtains the citrate, oxalate, malonate and the p-toluensulphonate of the ITA 362 and for which the analytical data is given in the examples which follow.

EXAMPLE 6

Preparation of the citrate of the ITA 362

The citrate is a yellowish, highly hydroscopic product.

m.p.: commences to soften at 52 deg. C., decomposing at 90° C.
Potentiometric evaluation of the basic groups: 103.4%

EXAMPLE 7

Preparation of the oxalate of the ITA 362 m.p.: 178–180 deg. C.
IR (KBr): characteristic bands at 1720 to 1700, 1475, 1455, 1255, 1165 and 1090 cm$^{-1}$.

EXAMPLE 8

Preparation of the malonate of the ITA 362 m.p.: 111–114 eg. C.
IR (KBr): characteristic bands at 1720–1600, 1490, 1455, 1090, 830 and 760 cm$^{-1}$.

EXAMPLE 9

Preparation of the p-toluensulphonate of the ITA 362 m.p.: 99–103 deg. C.
IR (KBr): characteristic bands at 3390, 1490, 1455, 1190, 1040, 1020, 820, 760 and 690 cm$^{-1}$.

Obviously, in connection with the above examples, all details which do not affect the essentiality of the invention may be varied without implying any limitation on the same.

The acute toxicity of the ITA 362 with both oral and intra peritoneal administration in the mouse and the rat has been studied using as reference the Amiodarona (The Merck Index, 9th edition., Merck Co., page 498, 1976) with administration under the same conditions.

The respective lethal dose 50 was calculated according to the method of Litchfield and Wilcoxon (Jl. Pharmacol. Exptl. 96 99, 1949). The values obtained are shown in the tables 1, and 2 given below.

TABLE 1

| Acute toxicity of ITA 362 in the rat and in the mouse, Oral administration. | | |
|---|---|---|
| Treatment | Species | $LD_{50}$ in mg/kg |
| ITA 362 maleate | Rat | >4000 |
| ITA 362 maleate | Mouse | >4000 |
| Amiodarona | Mouse | >4000 |

TABLE 2

| Acute toxicity of ITA 362 in the rat and in the mouse, Intraperitoneal administration. | | |
|---|---|---|
| Treatment | Species | $LD_{50}$ and confidence limits in mg/kg. |
| ITA 362 maleate | Rat | 105 (83–133) |
| Amiodarona | Rat | 885 (776–1010) |
| ITA 362 maleate | Mouse | 106 (102–110) |
| Amiodarona | Mouse | 940 (813–1086) |

In the Table 3 is shown the results of the vasodilatory activity of the ITA 362 in the perfusion test of the hindquarters of rats with a hyperpotasemic solution. (F. N. Fastier, F. M. Smirk. Jl, Pharmacolog. Exp. Therapy. 89. 256, 1947).

The activity turned out to be similar to that of the nitroglycerine which was used as the reference, thus demonstrating clearly the power of the compound.

The antiangina activity was also compared with that of the nitroglycerine by means of the amplitude increase protection test of the T wave for vasopression in the conscious dog. (A. Lindner, M. London, G. Werner, Scheiz. Med. Wsohr. 83, 360, 1953; J. Papp. L. Szekeres. Arch. Int. Pharmacodyn, 160, 1, 1966). The dose of 1 mg/kg with intravenous administration of the ITA 362 shows almost a 50% protection, its activity being greater than that of nitroglycerine which was used as the reference at a dose of 0.4 mg/kg. The results are shown in the Table 4.

Tables 5 and 6 show the anti-arrythmic activity of the ITA 362 in the male NMRI mouse by oral and intraperitoneal route using the fibrillation test by chloroform in the mouse. (V. W. Lawson, J. Pharmacol. Exp. Ther. 160, 22, 1968; B. Vargaftig, J. L. Coignet. Eur.J. Pharmacol. 6, 49, 1969).

In this test amiodarona was used as the reference and was compared with the activities of the various salts of the ITA 362. The activity of the two forms of maleate described in the example 4 were studied, with that in the table subtitled as isomer A corresponding to the first fraction obtained in the aforementioned example, and isomer B corresponding to the second fraction.

The calculated ED50 are similar, there being no significant statistical difference between either the two iosmers or in relation to the citrate. Table 6 illustrates that the activity is comparable to that of the amiodarona.

TABLE 3

Vasodilatory activity. Perfusion of the hind quarters of rats with a hyperpotasemic solution.

| Treatment | Concentration in g/ml | No. of Animals | % drop in pressure | $ED_{25}$ mg/kg |
|---|---|---|---|---|
| Nitroglycerine | $10^{-5}$ | 10 | 25.4 | $4.6 \cdot 10^{-6}$ |
|  | $10^{-6}$ | 16 | 24.7 | $r = 0.9590$ |
|  | $10^{-7}$ | 6 | 17.5 |  |
|  | $10^{-8}$ | 7 | 10.9 |  |
| ITA 362 citrate | $10^{-5}$ | 7 | 33.6 | $2.61 \cdot 10^{-6}$ |
|  | $10^{-6}$ | 20 | 16.3 | $r = 0.8605$ |
|  | $10^{-7}$ | 15 | 12.7 |  |
|  | $10^{-8}$ | 6 | 12.5 |  |

TABLE 4

Anti-angina activity. Amplitude increase protection of the T wave by vasopression in the conscious dog.

| Treatment | Weight kg. | Dose i.v. mg/kg | Control quot. treatment | t student | % Prot. |
|---|---|---|---|---|---|
| ITA 362 maleate | 14.0 ± 1.2 | 1 | 1.893 | $p < 0.025$ | 46.8 |
| Nitroglycerine at 1% | 15.3 ± 1.2 | 0.4 | 1.520 | n.s. | 28.9 |

TABLE 5

Anti-arrythmic acitivity. Fibrillation by chloroform in the male NMRI mouse. Route: p.o.

| Treatment | Dose. p.o. mg/kg | No. of animals | % protection versus fibrillation. | $ED_{50}$ and confidence limits $p < 0.05$ |
|---|---|---|---|---|
| Control | 25 ml/kg | 20 | 15 | — |
| ITA 362 citrate | 100 | 20 | 55 |  |
|  | 50 | 20 | 55 |  |
|  | 25 | 20 | 45 | 43.21 |
|  | 12.5 | 19 | 31.6 | (*) |
|  | 6.25 | 19 | 42.1 |  |
|  | 3.125 | 20 | 10 |  |
| ITA 362 maleate (isomer A) | 100 | 20 | 70 |  |
|  | 50 | 20 | 70 | 35.4 |
|  | 25 | 20 | 35 | (27.52 / 45.42) |
|  | 12.5 | 20 | 25 |  |
| ITA 362 maleate (isomer B) | 100 | 20 | 85 |  |
|  | 50 | 20 | 45 | 27.60 |
|  | 25 | 20 | 55 | (16.39 / 45.48) |
|  | 12.5 | 20 | 35 |  |

*calculation is not possible

TABLE 6

Anti-arrythmic activity. Fibrillation by chloroform in the male NMRI mouse. Route: i.p.

| Treatment | Dose i.p. mg/kg | No. of Animals | % protection versus fibrillation | $ED_{50}$ and confidence limits $p < 0.05$ |
|---|---|---|---|---|
| Control | 25 ml/kg | 20 | 5 | — |
| Amiodarona | 100 | 20 | 89.5 | 34.0 |
|  | 50 | 20 | 52.6 | (21.4 / 54.00) |
|  | 25 | 20 | 45 |  |
| ITA 362 citrate | 100 | 20 | 84.2 |  |
|  | 50 | 20 | 35 | 41.4 |
|  | 25 | 20 | 40 | (27.1 / 63.2) |
|  | 12.5 | 20 | 25 |  |
| ITA 362 maleate | 100 | 20 | 70 |  |
|  | 50 | 20 | 60 | 35.3 |
| (isomer A) | 25 | 20 | 35 | (20.17 / 61.98) |
|  | 12.5 | 20 | 35 |  |
| ITA 362 maleate (isomer B) | 100 | 20 | 95 |  |
|  | 50 | 20 | 70 | 24.50 |
|  | 25 | 20 | 35 | (16.11 / 37.20) |
|  | 12.5 | 20 | 40 |  |

It will be understood that each of the elements described above, or two or more together, may also find a useful application in other types of compounds differing from the types described above.

While the invention has been illustrated and described as embodied in a dioxolanic amine with pharmacological activity, its method of preparation, the pharmaceutical compositions containing same and their use in human medicine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Dioxolanic amine of the formula I

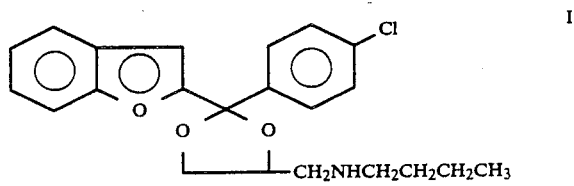

corresponding to the 2-(2'-benzofuranil)-4-n-butylaminomethyl-2-p-chlorophenyl-1,3-dioxolane, as well as its pharmaceutically acceptable salts such as maleate, citrate, orotate, oxolate, malonate, p-toluensulphate and the like.

2. A pharmaceutical composition useful in effecting intense vasodilatory, anti-angina and anti-arrhythmic activity, containing as active ingredient a vasodilating, anti-angina and anti-arrhythmic effective amount of the dioxolanic amine of its salt according to claim 1, in an acceptable pharmaceutical carrier.

3. The pharmaceutical composition according to claim 2, in the form of tablets, capsules, dragees or in suspension.

4. The pharmaceutical composition according to claim 2, further comprising non-toxic auxiliaries such as dispersal agents, compacting agents, emulsifiers, preservatives, or humectants.

5. A pharmaceutical composition useful for alleviation of symptoms associated with fibrillation and vasopression, containing as active ingredient a therapeutic effective amount of the dioxolanic amine or its salt according to claim 1, in an acceptable pharmaceutical carrier.

* * * * *